United States Patent [19]

Yiournas

[11] 4,276,879
[45] Jul. 7, 1981

[54] AUTOMATIC INJECTION APPARATUS

[75] Inventor: Costas Yiournas, Vineland, N.J.

[73] Assignee: Vineland Laboratories, Inc., Vineland, N.J.

[21] Appl. No.: 130,406

[22] Filed: Mar. 14, 1980

[51] Int. Cl.³ .............................................. A61M 5/00
[52] U.S. Cl. ..................................................... 128/218 A
[58] Field of Search ................... 128/218 A, 215, 216, 128/213, 224, DIG. 1, 218 R, 218 G, 253

[56] References Cited

U.S. PATENT DOCUMENTS

| | | | |
|---|---|---|---|
| 2,918,063 | 12/1959 | Tucker | 128/218 A |
| 3,641,998 | 2/1972 | Lyon et al. | 128/253 |
| 3,964,481 | 6/1976 | Gourlandt et al. | 128/218 A |
| 4,177,810 | 12/1979 | Gourlandt | 128/218 A |

Primary Examiner—John D. Yasko
Attorney, Agent, or Firm—Kenway & Jenney

[57] ABSTRACT

An improved automatic injection apparatus has a planar work surface with a hingedly attached retention plate which pivots from a raised position to a lowered position against the work surface in response to a member of an animal being forced against it to actuate a switch protruding through the work surface. Actuation of the switch operates a drive mechanism which forces a hypodermic needle attached to a syringe through an opening in the work surface and through an aligned aperture in the retention plate into the animal member, operates the syringe to inject a fluid into the animal, and then retracts the syringe and needle to the initial position. The retention plate is shaped to conform generally to the contours of the animal member and has oppositely facing restraining walls to accurately position the body member relative to the needle and to prevent lateral movement of the member during the injection process. The aperture in the retention plate is elongated to insure passage of the needle therethrough regardless of the inclination of the needle relative to the work surface.

3 Claims, 6 Drawing Figures

AUTOMATIC INJECTION APPARATUS

BACKGROUND OF THE INVENTION

This invention relates in general to apparatus for automatically injecting mature animals, especially birds, with a vaccine or other fluid substance. More particularly, the invention relates to an improved retention device for insuring proper positioning of the animal relative to the hypodermic needle of the apparatus while preventing premature actuation of the apparatus.

Automatic animal vaccinating devices are well known in the prior art. Typical examples of such devices are disclosed in U.S. Pat. Nos. 4,108,176 (Walden), 3,641,998 (Lyon et al.), 3,964,481 (Gourlandt et al.) and in U.S. Application Ser. No. 881,033, which is pending and has a common assignee with this application. The present invention is compatible for use with either of the systems disclosed in the latter two cases and, therefore, the contents of those cases are hereby incorporated by reference. Typically, the prior art devices function by the operator placing the animal alongside a positioning fixture and then actuating a switch, either manually or by forcing a portion of the animal's body against an actuator adjacent the positioning fixture. Generally, the positioning fixture accommodates various orientations of the animal's body to permit either subcutaneous or intramuscular vaccination.

Presently existing devices are suitable for use with very young animals, for example, with baby chicks which generally are inoculated within a few days of birth. Such animals are easy to manipulate into position and do not offer significant resistance to the operator. Also, in the specific case of baby chicks, the layer of feathers or down which covers the chick's body is relatively thin and closely conforms to the underlying tissue. Therefore, when the chick's body is pressed against the switch actuator with sufficient force to activate the syringe drive mechanism and to inject the hypodermic needle into the body, the needle will be injected into the muscle or skin of the bird and not merely into the feathers. The docile nature and small size of the bird also minimize any shifting of the bird during the injection process.

However, in the case of more mature birds, such as adult chickens or turkeys, the animal generally is much more active during the vaccination process and is not apt to remain still, but will fight the operator vigorously. In such a case, movements of the bird may cause the animal to be withdrawn from the location at which the needle protrudes, before the needle has effectively been injected into the skin or muscle and the fluid has been transferred. Also, in the case of a mature bird, the layer of feathers covering the skin is generally thicker and stiffer than in the case of the chick. This layer of feathers may offer sufficient resistance to actuate the switch and start the injection process before the underlying layer of skin is sufficiently close to the needle to insure effective penetration of the needle into the skin. In other words, there is the possibility that the needle will only penetrate the outer layer of feathers and not the underlying layer of skin, and that the fluid may be injected only into this feather layer, thereby invalidating the vaccination. Not only is this condition wasteful and, therefore, needlessly costly, but also the operator cannot be positive that the bird has been vaccinated properly.

The extended position of the outward end of the needle also must be essentially the same at each injection, to insure both effectiveness of the vaccination and the safety of the animal.

Therefore, it is an object of the present invention to position a violently struggling animal properly with respect to the vaccinating syringe to insure effective injection of the animal.

It is a further object of the present invention to insure that the automatic vaccination apparatus is actuated only when the portion of the animal's body to be injected is in sufficient proximity to the hypodermic needle to guarantee proper penetration of the needle into the animal and, thus, to prevent premature activation of the vaccination apparatus.

It is a still further object of the present invention to permit injection of the hypodermic needle into the animal at a wide range of angular inclinations without requiring modification or repositioning of the placement fixture.

It is a still further object of the present invention to insure repeatability of the amount of protrusion of the hypodermic needle beyond the retention plate, available for injection into the animal.

SUMMARY OF THE INVENTION

An automatic injecting apparatus, in accordance with the present invention, includes a housing having a planar work surface, a reservoir of fluid, and a hypodermic syringe supplied with fluid from the reservoir and having an attached hypodermic needle positioned opposite an opening in the work surface. The axis of stroke of the hypodermic needle is oriented at an acute angle with respect to the work surface. A syringe drive mechanism cyclically moves the syringe from a retracted to an extended position so as to reciprocate the needle through the opening, and operates the syringe while it is in the extended position. The syringe drive mechanism is cycled by a switch which has its actuating button protruding through the work surface adjacent the opening. A retention plate is hingedly joined at its bottom end to the work surface, and the retention plate is pivotable about this hinged joint from a lowered position at which it rests against the work surface. The retention plate has a planar bottom surface which conforms generally to the work surface when the retention plate is in the lowered position and a curved top surface which accepts the member of the animal to be injected. Side retaining walls extend upwardly from opposite sides of the curved top surface, and a spring member protrudes from the bottom surface to bias the retention plate away from the lowered position. The retention plate is located on the work surface so that an aperture in the retention plate is aligned with the opening in the work surface to allow passage of the hypodermic needle through the aperture. Lowering the retention plate to its lowered position causes the retention plate bottom surface to strike the actuating button of the switch to initiate the injection cycle.

In a specific embodiment of the present invention, the retention plate is contoured to more readily accept the various members of the animal's body to facilitate the proper positioning. Also, the retention plate aperture is elongated to present a more readily accessible target to the needle protruding through the work surface, thereby allowing clear passage of the needle through the aperture regardless of the angular inclination of the needle relative to the work surface and to the retention plate.

The objects and features of the invention will be more fully understood from the following detailed description which should be read in light of the accompanying drawings.

DESCRIPTION OF THE PREFERRED EMBODIMENT

Figure 1:
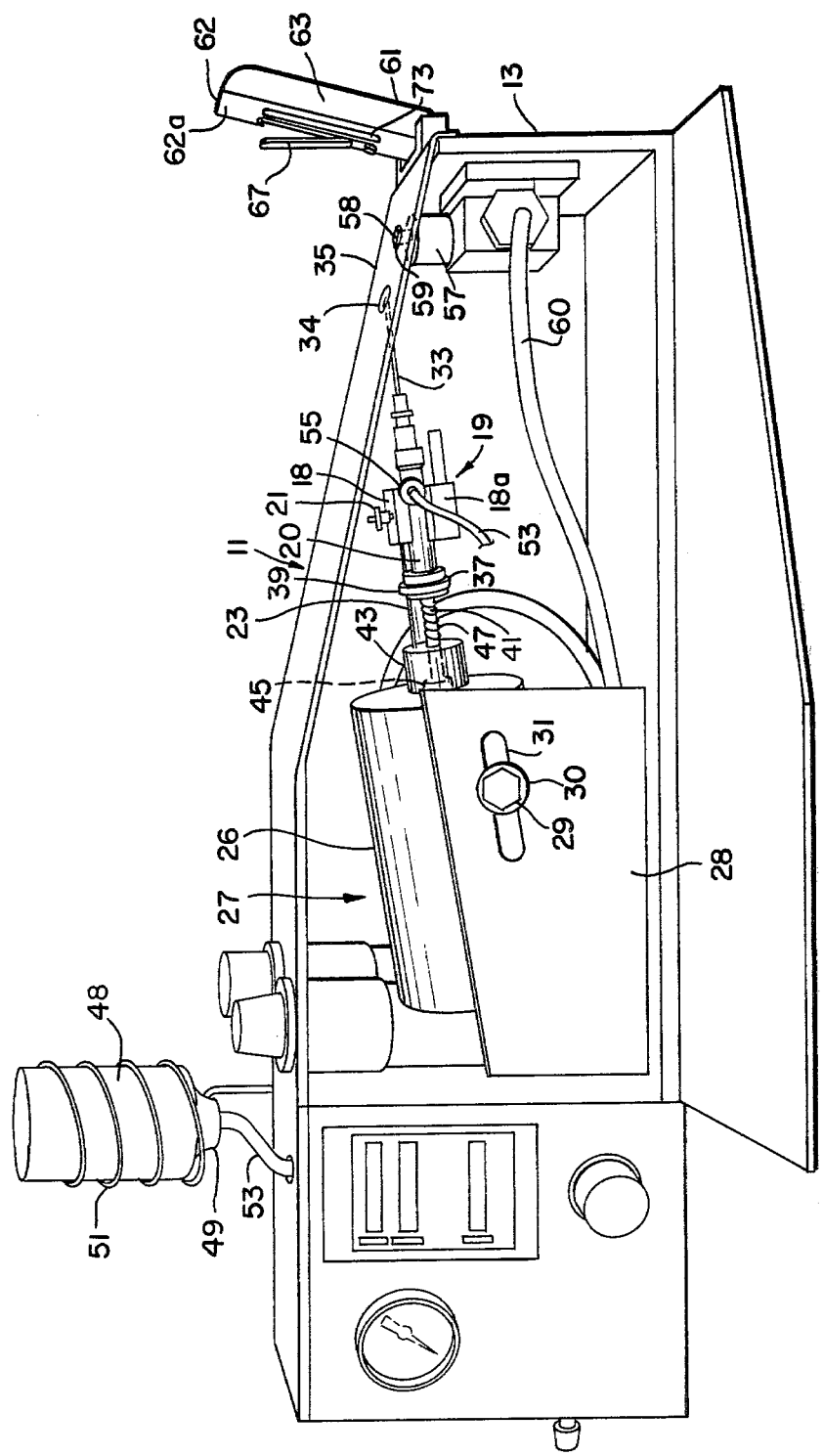
FIG. 1 is a side perspective view of an automatic injection apparatus in accordance with the present invention with the side panel removed to display the syringe and its associated drive mechanism.

In FIG. 1 an automatic injection apparatus 11 has an outer housing 13, a portion of which has been removed to expose the interior. A hypodermic syringe 20 is cradled securely in a mounting 19, loosely enough to allow axial movements of the syringe. A pressure-adjusting screw 21 bridges bifurcated segments 18, 18a of mounting 19 and controls the spacing therebetween. The screw can be tightened to draw the segments 18, 18a sufficiently close together to grasp the syringe for proper support and alignment, or can be loosened to separate these segments and permit disengagement of the syringe.

The mounting 19 is rigidly attached to the forward end of a guide rod 23 extending essentially parallel to a longitudinal axis of stroke of the syringe 20. One end of the guide rod 23 is welded to an outer housing 26 of an electric drive motor 27. The drive motor is supported within a U-shaped bracket 28 mounted on the housing 13, by means of a bolt 29 which passes through both a washer 30 and an elongated slot 31 formed in the bracket 28 and engages the outer housing 26. Tightening the bolt 29 against the washer and the bracket localizes the drive motor within the bracket, while loosening the bolt permits repositioning of the drive motor and the attached syringe. In the illustrated embodiment the slot 31 is oriented parallel to the axis of stroke to reposition the syringe therealong.

A hypodermic needle 33, attached to and outwardly extending from the forward end of the syringe 20 is aligned opposite an oval opening 34 in a sloped planar work surface 35, which surface forms a portion of the top of the housing 13. The needle 33 is parallel to the axis of stroke 25 of the syringe 20. The forward end of the needle 33 can protrude from the inside of the housing through opening 34 to penetrate the member of an animal (not shown) positioned above the opening. As previously mentioned, the syringe 20 can translate within segments 18 and 18a, and does so along the stroke axis. The forward movement of the syringe is limited by shoulder 37 of an annular collar 39 striking the rear surface of the mounting 19. This extended position of the syringe determines the amount of protrusion of the needle 33 through the opening 34. However, the drive motor can be moved within the bracket 28 as needed to adjust the amount of protrusion.

When protruding, the needle 33 forms an acute angle, typically between 15° and 40°, with the exterior of the planar work surface 35. This range of values is appropriate for both subcutaneous and intramuscular injections. Although the apparatus 11, as illustrated, is oriented in such a way that the planar work surface 35 is disposed more or less horizontally, it may be advantageous in certain situations to rotate the apparatus 90 degrees (in a direction toward the viewer) so that the planar work surface is in a vertical plane. It is intended that the apparatus function equally well in either orientation.

An operating plunger 41 of the syringe 20 communicates with the inner volume of the syringe, to force its contents outwardly through the needle 33 when the plunger 41 is driven forward along its axis. A coupling 43 joins the plunger 41 to the longitudinally aligned shaft 45 of the electric drive motor 27. Each time the drive motor is actuated, it reciprocates the shaft 45 longitudinally in a single forward-backward cycle, the length of the stroke being selected in advance. A spring 47 encompassing the plunger 41 is disposed between the coupling 43 and the collar 39. The spring constant of the spring is sufficiently large that the resistance to compression offered by the spring is greater than the oppositely directed retaining force produced by the segments 18 and 18a gripping the body of the syringe 20. In other words, as the drive motor drives the shaft 45 forward, the forward motion is transferred to the entire syringe, since the spring maintains the initial spacing between the coupling and the collar, and prevents actuation of the plunger. However, when the shoulder 37 strikes the fixed mounting 19, and the syringe occupies its extended position, the still-moving shaft and coupling compress the spring, and drive the plunger into the stationary syringe.

A bottle 48 of the fluid being injected is suspended, with its opening 49 downward, in a frame 51 mounted to the housing 13. A tubing 53 coupled to the opening 49 extends downwardly to gravity-feed the fluid into a supply inlet 55 of the syringe. The inlet communicates with the internal volume of the syringe so that the syringe is replenished automatically with fluid as the plunger is withdrawn by the return (i.e. rearward) stroke of the shaft 45, and the syringe is returned to its rearwardmost, or retracted, position.

Figure 2:
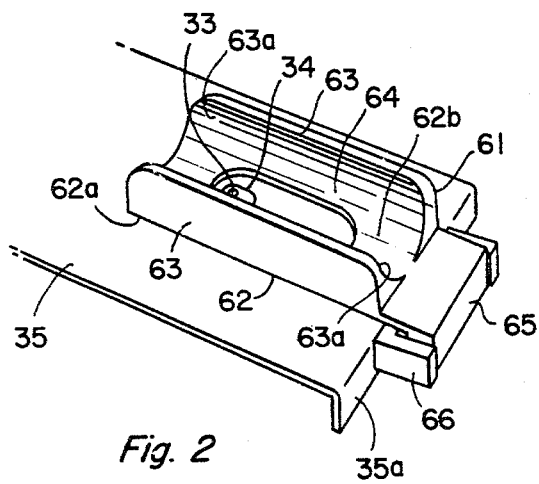
FIG. 2 is a side perspective view of the retention plate.

A switch 57 for cycling the electric drive motor is positioned beneath the sloped work surface 35 with its actuating button 58 protruding slightly through a hole 59 in the work surface 35 beneath a retention plate 61. A protrusion of about 1/16 inch is typical. An electrical cable 60 links the switch 57 to the drive motor 27. Referring also to FIG. 2, the retention plate 61, whose purpose is to position and orient an animal member at the appropriate location relative to the hypodermic needle 33, is a generally rectangular-shaped receptacle having a base portion 62 with a planar bottom surface 62a which conforms exactly to the planar sloped work surface when the retention plate rests thereon. Two side retaining walls 63 extend perpendicularly upward from the planar bottom surface 62a and the inwardly facing surfaces 63a of these retaining walls join a curved top surface 62b of the base portion 62 to present a continuous, cylindrically curved interior surface 64. The forward and rear ends of the retention plate 61 are not enclosed, thereby forming a trough to facilitate insertion of an animal member therein. The configuration of the retention plate 61 serves to properly seat an animal member, and once it is seated, to prevent lateral displacement of the member until the completion of the injection. The configuration just described is particularly suitable for accommodating the neck portion of an adult chicken or turkey. The specific contour of the interior surface 64 can be modified as appropriate for the body member or the animal to be engaged.

The retention plate 61 may be machined, cast or otherwise formed from a material which yields a strong, rigid structure. The rigidity insures that no significant deformation or flexing of the retention plate occur despite the forces being applied to it during use. Integrally formed with the underside of the forward end of the base portion 62 is a flange 65. The flange 65 pivotally engages a junction block 66 which is rigidly attached to a downwardly extending edge 35a of the planar work surface 35. The flange 65 is arranged within the junction block so that the retention plate can pivot from a lowered position at which it lies flush against the planar work surface 35 to a raised position at which it is generally perpendicular to the surface 35 (see FIG. 1). The mounting of the retention plate 61 at the forward end of the surface 35 is important to negate flexing of the surface 35 during vaccination. Such flexing may affect adversely the positioning of the animal relative to the needle at the moment of injection. Generally, because of hygienic concerns, the surface 35 is fashioned of a highly polished stainless steel, usually of a light gauge. By pivotally mounting the retention plate to the surface 35 at a location where it is supported from underneath, the force exerted by the plate against the surface will be counteracted.

Figure 4:
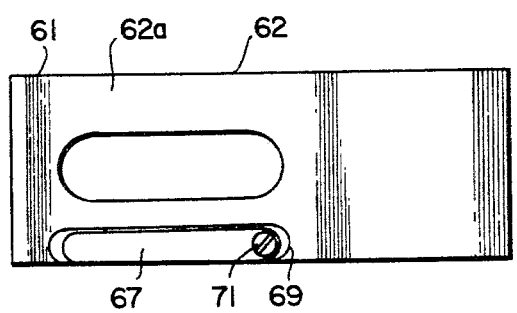
FIG. 4 is a bottom view of the retention plate as mounted on the work surface.
Figure 5:
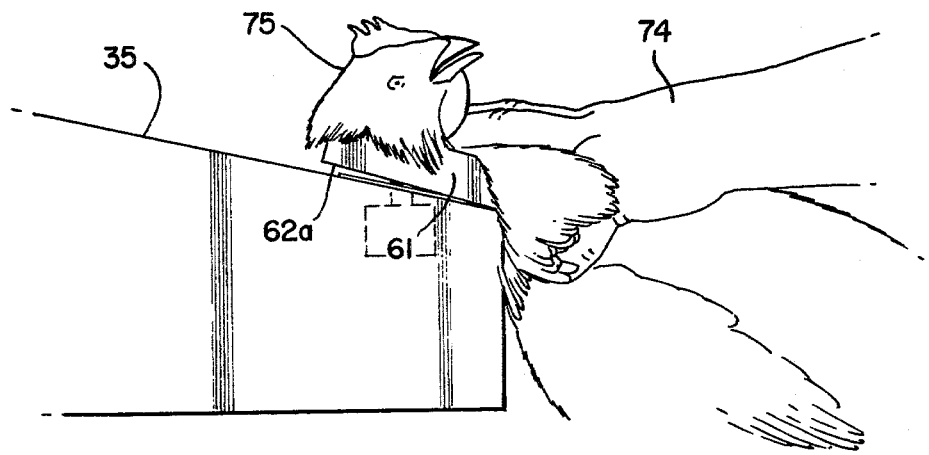
FIG. 5 is a side elevation view of the retention plate, with an animal member engaged therein, in its at-rest, upwardly biased position.

Referring now to FIGS. 4 and 5 a leaf spring 67 attaches at one end by a screw 71 to a recess 69 formed in the bottom surface 62a of the retention plate. The other end of the spring 67 extends beyond the plane of the bottom surface 62a. This spring 67 maintains the retention plate 61 in a normal at-rest position in which it is slightly raised above the planar work surface 35 (see FIG. 5). The spring elevates the retention plate to a height such that the flat bottom surface 62a of the plate 61 does not contact the protruding button 58 of the switch 57. The spring constant of the spring is selected to provide a predetermined amount of resistive force to insure that an appropriate threshold of downward force must be exceeded before the plate moves to its fully lowered position and thereby actuates the switch.

Figure 3:
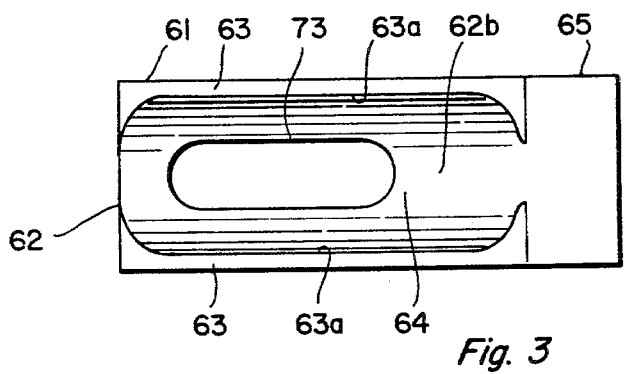
FIG. 3 is a top view of the retention plate.

As shown in FIG. 3, the retention plate 61 has a broad oval-shaped aperture 73 through the base portion, which aperture is elongated in the front-to-rear direction of the plate. The aperture 73 is located such that when the plate is in its lowered position the hypodermic needle 33 can extend unimpededly through the opening 34 in the planar work surface 35 (See FIG. 1) and through the retention plate into contact with the animal regardless of the angular orientation of the needle relative to the work surface 34.

Figure 6:
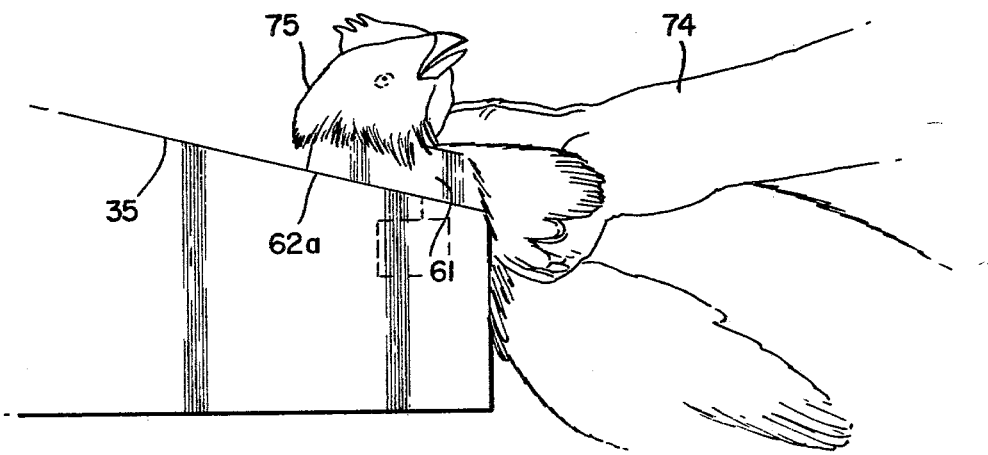
FIG. 6 is a side elevation view, similar to FIG. 5, showing the retention plate in its lowered position resting against the work surface.

Referring now to FIGS. 5 and 6, the typical operation of the injection apparatus proceeds as follows. An operator 74 places a member of an animal 75 to be injected, here the neck of a chicken, within the appropriately curved contour of the upwardly biased retention plate 61 (see FIG. 5). Once the animal is properly positioned, the operator applies a downward force against the animal member. Sufficient force to counteract the upward bias of the leaf spring is applied to the retention plate only when a relatively solid portion of the animal's body makes contact with the plate. For example, a resilient layer of feathers will not be able to transfer enough force to move the retention plate downwardly, but rather it will become compressed by the oppositely applied forces generated by the spring and the operator's hand respectively. Only when the substantial resistance offered by the firm tissue of the body member acts on the retention plate, does the plate begin to lower. Because of the slight protrusion of the actuator button above the planar work surface, the entire bottom surface 62a of the retention plate must be in intimate contact with the planar work surface 35, as in FIG. 6, before the switch is fully actuated. The bottom surface actually touches the actuator button at a height of several thousandths of an inch above the planar work surface, but this same several thousandths of an inch of travel is needed to close the internal contacts of the switch.

Once actuated, the switch 57 cycles the electric drive motor 27 to drive the syringe 20 and attached needle 33 from the retracted position to the extended position. The needle 33 passes through the opening 34 and the aperture 73 into the animal member, and the syringe operates to transfer the fluid into the animal tissue. The return stroke of the drive motor returns the syringe and needle to the retracted position and refills the syringe with the fluid.

It can be readily seen that the rigid, inflexible structure of the retention plate insures that the plate is always in its downwardmost position before the needle passes therethrough. Thus the amount by which the needle protrudes above the retention plate is essentially constant injection after injection. The apparatus as described repeatedly can produce a protrusion accurate to within ±1/32 inch. This repeatability is important for effective, safe vaccination of the animal. Also the positive downward displacement of the plate needed to actuate the switch and the accompanying sudden stop as it hits the planar work surface give the operator an easily detectable and reliable indication that the injection has taken place. This avoids either multiple-injection or non-injection of the animal.

Although the preceding description of the preferred embodiment is described in terms of an electrical drive system the apparatus is adaptable to a variety of conventional drive systems including for example, a hydraulic or a pneumatic system as disclosed in the above-mentioned application Ser. No. 881,033.

Those skilled in the art readily recognize that various modifications may be made to the structures disclosed in the specification and the accompanying drawings without deviating from the basic operating principles of the present invention. Different placements of the basic components relative to one another will become obvious depending on the orientation most appropriate for the vaccinating situation at hand. Such modifications are intended to fall within the scope of the appended claims.

What is claimed is:

1. In an automatic apparatus for injecting fluids into animals, having:
   a housing having a planar work surface;
   a reservoir of fluid;
   a hypodermic syringe supplied with fluid by said reservoir, the hypodermic needle of said syringe being positioned opposite an opening in said planar work surface, the axis of stroke of said hypodermic needle being at an acute angle with respect to said work surface;

syringe drive means for cyclically moving said syringe from a retracted to an extended position so as to reciprocate said needle through said opening, said drive means actuating said syringe while in said extended position;

switch means for cycling said syringe drive means, the actuating member of said switch means protruding through said work surface adjacent said opening; the improvement comprising:

a rigid retention plate hindedly joined at its bottom end to said work surface, said retention plate being pivotable about said hinged joint from a lowered position against said work surface, said retention plate having, a planar bottom surface which conforms generally to said planar work surface when said retention plate is in said lowered position, a cylindrically curved top surface for accepting the animal member to be injected, side retaining walls extending upwardly from opposite sides of said planar bottom surface, a spring member for biasing said retention plate away from said lowered position, and an elongated aperture through said retention plate, said retention plate being located on said sloped surface whereby said aperture is aligned with said opening to allow passage of said needle therethrough, and whereby lowering said retention plate to said lowered position causes said retention plate botton surface to operate said actuating member of said switch means.

2. Apparatus as set forth in claim 1, wherein said side walls have inwardly facing surfaces which are curved to form a continuous U-shaped surface with said curved top surface.

3. Apparatus as set forth in claim 1 wherein said retention plate bottom surface operates said actuating member only when said bottom surface is resting substantially against said planar work surface.

* * * * *